United States Patent [19]

Nielsen et al.

[11] Patent Number: 4,560,651

[45] Date of Patent: Dec. 24, 1985

[54] DEBRANCHING ENZYME PRODUCT, PREPARATION AND USE THEREOF

[75] Inventors: Grethe C. Nielsen, Tastrup; Ivan V. Diers; Helle Outtrup, both of Vaerlose; Barrie E. Norman, Farum, all of Denmark

[73] Assignee: Novo Industri A/S, Denmark

[21] Appl. No.: 434,745

[22] Filed: Oct. 18, 1982

Related U.S. Application Data

[63] Continuation-in-part of Ser. No. 255,952, Apr. 20, 1981, abandoned.

[51] Int. Cl.[4] .................... C12P 19/22; C12P 19/20; C12P 19/16; C12N 9/44; C12N 1/20; C12R 1/07
[52] U.S. Cl. ........................................ 435/95; 435/96; 435/98; 435/210; 435/253; 435/832
[58] Field of Search ................... 435/96, 98, 253, 210, 435/95

[56] References Cited

U.S. PATENT DOCUMENTS 4,011,139 3/1977 Horwath et al. ................ 435/210
4,211,842 7/1980 Marshall ........................... 435/210

OTHER PUBLICATIONS

Ueda et al., Journal of Fermentation Technology, vol. 49, No. 6, pp. 552–558, (1971).
Morgan et al., Journal of Applied Bacteriology, vol. 46, pp. 291–294, (1979).
Bull, editor, Progress in Industrial Microbiology, vol. 15, pp. 127–150, (1979).

Primary Examiner—Lionel M. Shapiro
Attorney, Agent, or Firm—Fidelman, Wolffe & Waldron

[57] ABSTRACT

A novel debranching enzyme product with properties in terms of thermostability and pH-optimum comparable to those of glucoamylase is produced by cultivating a strain belonging to the novel taxonomic group *Bacillus acidopullulyticus*. The novel debranching enzyme is used in conjunction with known saccharifying enzymes for the hydrolysis of starch.

12 Claims, 3 Drawing Figures

FIG. 1

ACTIVITY OF PURIFIED PULLULANASE AT DIFFERENT pH AND TEMPERATURES
(30 MINUTES REACTION TIME)

DEBRANCHING ENZYME PRODUCT, PREPARATION AND USE THEREOF

This is a continuation-in-part of Ser. No. 255,952, filed Apr. 20, 1981, now abandoned.

This invention is within the field of enzymes for the enzymatic conversion of starch to sugars. More specifically, the present invention relates to a novel debranching enzyme product capable of hydrolyzing alpha-1,6-glycosidic bonds in amylopectin and pullulan. This novel enzyme product may be classified as a debranching enzyme of the pullulanase type. The invention is also directed towards a process for preparing the novel debranching enzyme product and to the use thereof for the conversion of starch into dextrose and/or maltose containing starch hydrolysates, such as dextrose and maltose syrups.

The enzyme product of this invention comprises at least one of the multiplicity of debranching enzymes produced by various strains of *Bacillus acidopullulyticus*, which enzymes have been found to differ one from the other in immunochemical and enzymatic properties.

BACKGROUND OF THE INVENTION

During the past decade the all-enzymatic hydrolysis of starch to syrups has gained wide and steadily increasing acceptance within the starch processing industry. On a world-wide basis the present enzymatic production of dextrose syrup from starch is estimated to exceed 3 million tons (calculated as dry substance) per annum compared with about 0.4 million tons ten years ago.

The process generally adopted for enzyme—enzyme hydrolysis of starch encompasses the sequential steps of liquefaction and saccharification, the former being catalysed by an alpha-amylase, such as the thermostable *B. licheniformis* alpha-amylase, e.g. TERMAMYL ® supplied by NOVO Industri A/S, Denmark, and the saccharification to dextrose (D-glucose) being effected in the presence of a glucoamylase, usually of fungal origin, such as AMG-150 L, also obtainable from the above named company. Obviously, the dextrose syrup producer aims at obtaining the highest possible yield of dextrose with the least possible expenditure of enzymes and of energy.

The highest dextrose level attainable by the conventional process, starting with 30-40 percent (by weight) starch suspension and saccharifying at 30 percent dry solids (D.S.), is about 96 percent (by weight) dextrose (96 DX). The reasons why the conventional starch conversion process does not proceed appreciably beyond that limit are essentially twofold.

Firstly, amylopectin (which constitutes about 80% of the majority of industrially important starches, including that of corn or maize), exhibits a branched chain structure in that it contains a significant number of alpha-1,6-glycosidic bonds. Whereas amylopectin is only partially degraded by alpha-amylase because alpha-amylase is practically devoid of alpha-1,6-glucosidase activity, substantial hydrolysis of the branched oligosaccharides including alpha-limit dextrins occurs in the subsequent saccharification step catalyzed by glucoamylase which also hydrolyses alpha-1,6-glycosidic links. However, the latter reaction proceeds at a considerably lower rate than the corresponding hydrolysis of alpha-1,4-bonds, whereby complete saccharification is impeded. Attempts to remedy the situation by adding more glucoamylase collides with a second obstructive feature (apart from incurring higher enzyme costs), namely the ability of glucoamylase also to catalyze dextrose polymerization (the so-called reversionary reaction).

It should be mentioned in passing that an increase of starch conversion from about 96 DX to about 98 DX (which for certain uses of dextrose is regarded as a highly significant improvement) entailing thereby a reduction in the content of non-dextrose contaminants by about 50 percent, can be achieved by employing a relatively high level of glucoamylase combined with a dilution of the substrate to about 15 percent D.S., vide U.S. Pat. No. 4,017,363. However, the subsequent concentration of such a dextrose solution to the higher conventional dry solids levels is energy consuming.

The prior art has suggested employment of glucoamylase and a debranching enzyme simultaneously to obtain a significant increase in dextrose level, the rationale being that debranching enzymes have been shown to efficiently hydrolyse specific types of alpha-1,6-glycosidic bonds occurring in branched chain oligosaccharides, and certain alpha-limit dextrins. In this respect reference is made to U.S. Pat. No. 3,897,305 disclosing the combined use of glucoamylase and *Aerobacter aerogenes* (*Klebsiella pneumoniae*) pullulanase, whereby a significant increase in DX of up to 2 percent can be achieved for syrups containing at least 30 percent D.S. Similar results have been demonstrated for the combined action of glucoamylase and another debranching enzyme, viz. *Pseudomonas amyloderamosa* isoamylase as described in British Patent Application No. 8107287.

However, in the first instance practically no saving of glucoamylase is achieved because the pH optimum of *K. pneumoniae* pullulanase makes it mandatory to conduct the saccharification at a relatively high pH (5,5-6) whereat the activity of glucoamylase is dramatically reduced.

The same problem is not encountered with the isoamylase which has a pH optimum much closer to that of glucoamylase, whereby the dosage of the latter can be substantially reduced (by about 50 percent), simultaneously with the attainment of an increase in DX value of 1-2 percent. However, a serious drawback of the isoamylase process (and actually shared by the known pullulanase process as well) is the heat lability of the debranching enzymes known in the art. This has meant that heretofore no saccharification in the presence of debranching enzyme has been technically feasible above about 55° C., whereas glucoamylase per se is adequately stable even at 60° C. at which temperature level the risk of microbial contamination of substrates is significantly reduced as compared with lower temperatures.

Obstacles akin to those described hereinbefore have been encountered in the conversion of starch to high maltose syrup by means of beta-amylases. Like the alpha-amylases, beta-amylases are only capable of partially degrading amylopectin, in that hydrolysis thereof stops as an 1,6-alpha-branch point is approached. By combining the action of beta-amylase with that of a debranching enzyme, such as pullulanase or isoamylase, a substantial increase in maltose content can be achieved as disclosed in British Pat. No. 1.144.950 and U.S. Pat. No. 3,677,896. However, again saccharification temperatures above 55° C. are not feasible due to the heat lability of the debranching enzymes, whereby the risk of bacterial contamination is substantially increased.

It is an object of the present invention to obviate the shortcomings of the debranching enzymes known heretofore by furnishing a novel debranching enzyme having a temperature stability comparable to that of glucoamylase, and furthermore, possessing a pH optimum close to that of glucoamylase.

The invention resides in the surprising discovery that a novel debranching enzyme of the pullulanase type having such properties is produced by newly discovered microorganisms of the genus Bacillus belonging to the taxonomic group as hereinafter defined.

SUMMARY OF THE INVENTION

According to its first aspect the present invention provides a debranching enzyme product which comprises a novel debranching enzyme of the pullulanase type having the following characteristics:

(a) it is obtainable from a fermentation broth produced by cultivating in a suitable nutrient medium a strain of the taxonomic group herein named *Bacillus acidopullulyticus*, (b) it exhibits enzyme chemical properties essentially identical to and immunochemical properties identical or partially identical to those of the debranching enzyme derived from the Bacillus strain NCIB 11607, (c) its activity optimum, measured by incubation for 30 minutes in acetate buffer (0.05M) at pH 4–5 is at least about 60° C., (d) its pH optimum is in the range of 3.5 to 5.5 as determined by incubation for 30 minutes in acetate buffer (0.05M) at about 60° C., and (e) it has a residual activity after 72 hours at 60° C. as measured in a dextrose solution (30 percent D.S. by weight) at pH 5 of at least 50 percent.

The debranching enzyme product may be in solid or liquid form and will generally have an activity in the range of from 10 to 350,000 pullulanase units (as hereinafter defined) per g.

In a preferred embodiment of the present invention the activity of the debranching enzyme product is in the range of from 100 to 15,000 pullulanase units per g.

According to a further aspect of the present invention there is provided a process for the preparation of a debranching enzyme product comprising a debranching enzyme, which enzyme exhibits an activity optimum at about 60° C. or above, a pH optimum in the pH-range of 3.5 to 5.5, and good thermostability at 60° C., which process comprises the cultivation in a suitable nutrient medium containing carbon and nitrogen sources and inorganic salts, of a debranching enzyme producing Bacillus strain belonging to the taxonomic group herein named as *Bacillus acidopullulyticus*, followed by recovery of said debranching enzyme product by conventional means.

In a most preferred embodiment of preparing the debranching enzyme product of this invention the *Bacillus acidopullulyticus* strain is selected from the group consisting of NCIB 11607, NCIB 11610, and the mutant strains NCIB 11638 and NCIB 11647, the latter two being the more preferred.

In another preferred embodiment the *Bacillus acidopullulyticus* strain is NCIB 11611.

In another preferred embodiment the *Bacillus acidopullulyticus* strain is selected from the group consisting of NCIB 11636 and NCIB 11637.

In an additional most preferred embodiment the *Bacillus acidopullulyticus* strain is selected from the group consisting of NCIB 11639 and a mutant therefrom, NCIB 11777.

According to still another aspect, the present invention provides a process for converting starch into syrups containing dextrose and/or maltose, which process comprises conducting the saccharification, optionally but preferably preceded by a liquefaction step to form a starch hydrolysate, in the presence of an enzyme system which comprises effective amounts of the novel debranching enzyme product as defined hereinbefore and a saccharifying enzyme selected from the group consisting of glucoamylase and beta-amylase.

In a preferred mode of using the debranching enzyme of this invention the dry solids content of the starch hydrolysate is at least 30 percent by weight, the saccharification thereof being conducted in the pH-range of from 3.5 to 5.5 at a temperature in the range of from 55° C. to 65° C. Preferred dosages of glucoamylase and beta-amylase are in the range of from 0.05 to 0.5 AG units and from 0.005 to 0.3 beta-amylase units, respectively, the preferred dosage of debranching enzyme being in the range of from 0.005 to 5 pullulanase units (as hereinafter defined), per g of dry solids in the starch hydrolysate.

In an additional preferred mode the saccharifying enzyme is glucoamylase, whereby starch is converted into high DX dextrose syrup.

DETAILED DESCRIPTION OF THE INVENTION

Bacillus acidopullulyticus

In the foregoing summary of the invention, the microorganism productive of this enzyme has been identified as *Bacillus acidopullulyticus*, an identification which normally is the genus and species designation of a taxonomic category. In this instance, however, the identification is intended to refer to a taxonomic group. The term "taxonomic group" (as defined in the 1976 Revision of the Bacteriological Code) refers to any group of organisms treated as a named group in a formal taxonomy and may or may not correspond to a category.

The inventors herein have not, as of the date hereof, satisfied all the requirements for establishing *Bacillus acidopullulyticus* as a new species of microorganism (i.e., a category). In addition, they have reason to believe that the taxonomic group *Bacillus acidopullulyticus* includes at the minimum a single species, and one or more variants therein, or else two or more closely related species.

The novel microorganisms have been characterized in sufficient detail to satisfy the usual requirements for identification within a category. However, they fail to fall into any recognized catagory, but have sufficient number of characteristics in common for placement into a single taxonomic group, the taxonomic group herein named *Bacillus acidopullulyticus*.

In taxonomy, immunochemical methods are increasingly used as a tool to measure structural similarities among homologous proteins to assess natural relationships between organisms that possess isofunctional enzymes.

The reasoning behind this is that the homology of isofunctional enzymes will increase, the closer related the organisms are. In some instances isofunctional enzymes e.g. extracellular serine proteases are identical within a species, in other instances the homology is only partial e.g. when an enzyme may appear in several forms due to allosteric variation or the presence of forms of the enzyme in which a terminal part of the amino acid sequence has been split off.

In some instances there may be extensive homology with isofunctional enzymes from closely related species, e.g. alpha-amylase from *B. amyloliquefaciens* and *B. Licheniformis*.

The degree of homology is determined by the amino acid sequence in question. Unfortunately this sequence is not known for the debranching enzymes of this invention. Immunochemical test methods may be a good substitute because the number of common antigenic determinants is a good measure of the degree of homology in the amino acid sequences.

It has been found that the debranching enzymes of the strains of *Bacillus acidopullulyticus* all show substantial immunochemical identity to the enzyme of the type strain. In some of the enzymes complete identity has been found, in other enzymes only partial identity has been found. No identity has been found with debranching enzymes from Bacillus species of other known microorganisms such as *B. megaterium* and *B. cereus*. This is taken as a strong reason to believe that the organism strains herein described are closely related and should be classified together as a separate taxonomic group, i.e. the taxonomic group *Bacillus acidopullulyticus*.

The Microorganisms

Isolation: The microorganisms productive of the debranching enzyme of the present invention were selected by means of their ability to grow on a basal medium prepared by aseptic admixture of equal volumes of tryptone solution (1 percent) and a salt solution of the following composition:

| Salt | Percent |
| --- | --- |
| $(NH_4)_2 SO_4$ | 0.04 |
| $MgSO_4, 7H_2O$ | 0.1 |
| $CaCl_2, 2H_2O$ | 0.05 |
| $KH_2PO_4$ | 0.6, | the pH of the salt solution being adjusted to 3 with sulphuric acid (10N) prior to heat sterilization. The pH of the final basal medium was 4.8–5.2.

Agar substrates were prepared from the basal medium containing pullulan or amylopectin (0.5 percent), with or without yeast extract (1 percent). Incubation was conducted at 30° C.–37° C. Pullulanase activity was detected as clearing zones following precipitation of pullulan by covering the agar plates with acetone. Debranching of amylopectin was detected as zones of hydrolysis exhibiting a strong blue colour with iodine-potassium iodide reagent.

A number of microbial isolates from natural sources, particularly from soil samples, were selected according to the above screening procedure and, when subjected to further tests as hereinafter described, shown to produce the enzyme of the present invention. Examples of such cultures and mutants thereof were deposited with the National Collection of Industrial Bacteria, Torry Research Station, Aberdeen, Scotland and accorded the reference numbers indicated in the following table I.

TABLE I

| NCIB NO. | Date of Deposition | Origin |
| --- | --- | --- |
| 11607 | 8th Sept., 1980 | Soil from Zoo, Penang, Malaysia |
| 11610 | 8th Sept., 1980 | Soil collected in Rio de Janeiro |
| 11611 | 8th Sept., 1980 | ibidem |
| 11636 | 17th Febr., 1981 | Soil from citrus plantation, Jamaica |
| 11637 | 17th Febr., 1981 | ibidem |
| 11638 | 17th Febr., 1981 | Mutant of NCIB 11607 |
| 11639 | 17th Febr., 1981 | Soil collected in Hillerod, Denmark |
| 11647 | 7th April, 1981 | Mutant of NCIB 11607 |
| 11777 | 29th September, 1982 | Mutant of NCIB 11639 |

Taxonomy

The newly discovered microorganisms of the invention are aerobic, rod shaped and endospore forming bacteria. They therefore belong to the genus Bacillus.

Their properties do not fit any of the recognized species of the genus Bacillus as described in Bergey's Manual (VIIIth Edition, Williams and Wilkins, Baltimore, 1974), or the monograph: The Genus Bacillus, by Gordon, Heynes and Pang, Agriculture Handbook No. 427, US Department of Agriculture, 1973. The present inventors therefore classify them as a new taxonomic group to which the name *Bacillus acidopullulyticus* has been accorded.

The diagnosis of this novel taxonomic group is as follows:

| Morphology: | |
| --- | --- |
| Vegetative cells: | Rods with a diameter of 0.6–1 micron. Swollen cells of protoplast character are frequently observed and seem to be stable during several hours of submerged fermentation. |
| Spores: | Cylindrical to ellipsoid, central to subterminal, sporangia not swollen. In phase contrast microscopy the spores are difficult to distinguish from unstainable globules which may be present in the protoplasm. Contrary to these globules the spores are stained by malachite green. |
| Biochemical reactions: | |
| Gram reaction | positive |
| Catalase | positive |
| Aerobic growth | positive |
| Anaerobic growth | negative |
| Growth at 50° C. | negative |
| Growth at 30° C.–37° C. | good |
| Growth in 3.5% NaCl | negative |
| Growth at pH 4.8–5.2 in basal medium (vide supra) containing pullulan as carbon source | good |
| Egg-yolk reaction | negative |
| Acid from: | |
| glucose | positive |
| mannitol | positive |
| Reduction of nitrate to nitrate | positive |
| Use of citrate | negative |
| Use of propionate | negative |
| Decomposition of tyrosine | negative |
| Production of a starch debranching pullulanase active at 60° C. in the pH-range from 3.5 to 5.5: | positive |

| | |
|---|---|
| -continued | |
| VP reaction | variable |
| Hydrolysis of casein | variable |
| Acid from: | |
| xylose | variable |
| arabinose | variable |

The morphology of the new debranching enzyme producing strains indicates that they belong to the morphological group I of the genus Bacillus.

A type culture of the new taxonomic group is NCIB 11607.

Other representative strains of the group are NCIB 11610, 11611, 11636 and 11637, and 11639.

A variety of Bacillus species are known producers of pullulan-hydrolysing enzymes (Progress in Industrial Microbiology, vol. 15 (1979), and Morgan F. J., Adams K. R., and Priest F. G.: J. Appl. Bacteriol. 46 p. 291 (1979)). However, none of the known species of Bacillus produce a pullulanase retaining its activity at 60° C. at pH below 5.0.

Hence, according to an additional aspect of the present invention there is provided a biologically pure culture of a bacterium belonging to the novel taxonomic group of *Bacillus acidopullulyticus* as hereinbefore defined.

Determination of Pullulanase Activity

One pullulanase unit (PU) is defined as the amount of enzyme which under standard conditions (temperature 60° C. and pH 5.0) hydrolyses pullulan at a rate corresponding to the formation of reducing groups equivalent to $1\mu$ mole of glucose per minute.

A 4 percent by weight solution (1 ml) of pullulan (supplied by Sigma Chemical Co.) in acetate buffer (0.1M, pH 5) is preheated for 10 minutes at 60° C. followed by addition of a solution (1 ml) of the enzyme dissolved in deionised water at a concentration corresponding to 0.04–0.15 PU per ml. The reaction is stopped after 30 minutes by addition of carbonate buffer, pH 10 (3 ml of 0.5M). The concentration of reducing groups liberated is then determined by means of the Somogyi-Nelson method (J. Biol. Chem. 153 (1944) 375–80; Ibid. 160 (1945) 61–68).

Preparation of debranching enzyme product

A Bacillus strain capable of producing the debranching enzyme product of the present invention is usually propagated on a solid substrate prior to its cultivation under aerobic conditions in a suitable fermentation medium. Both media contain assimilable sources of carbon (e.g. glucose for liquid and amylopectin for solid media), a basal salt composition (vide supra) comprising e.g. ammonium sulphate as the nitrogen source, together with growth promoting nutrients, such as yeast extract and/or corn steep liquor (liquid medium) or tryptone (solid substrate). The fermentation is typically conducted at slightly elevated temperature, generally in the range of from 30° C. to 35° C. and at a pH below 6, preferably in the range of 5.0–6.0 and preferably kept approximately constant by automatic means. The enzyme is excreted into the medium.

The ensuing fermentation broth, usually containing from about 0.1 to about 50 PU per ml, may be freed of bacterial cells, debris therefrom together with other solids, for example by centrifugation. The supernatant containing the enzyme may be further clarified, for example by filtration or centrifugation, and then concentrated as required, for example by ultrafiltration or in an evaporator under reduced pressure to give a concentrate which, if desired, may be taken to dryness, for example by lyophilization or spray-drying. Typically, the resulting crude enzyme product exhibits an activity in the range of from 100 to 15,000 PU per gram.

Purification of Debranching Enzyme

The debranching enzyme product of the present invention may be purified from a crude enzyme product, such as the concentrate obtained in Example 2 hereinafter, for example by a combination of cation and anion exchange chromatography.

A column of CM-Sepharose CL-6B was equilibrated with a phosphate-citrate buffer (0.05M $Na_2HPO_4$ titrated with 0.05M citric acid to pH 4.5). The enzyme concentrate was diluted with water to the same conductivity as the equilibrating buffer and the pH was adjusted to 4.5. The sample was then applied to the column whereby the enzyme was completely adsorbed. Elution was conducted with the same buffer linearly admixed in a gradient mixer with 0.05M solution of $Na_2HPO_4$ so as to provide a gradient in pH. The fractions were analysed for pullulanase activity by the method described hereinbefore and for protein content by the Lowry method (J. Biol. Chem. 193 (1951) 256), and fractions showing enzyme activity were pooled.

A column of DEAE-Sepharose CL-6B was equilibrated with phosphate-citrate buffer (0.01M $Na_2HPO_4$ titrated with 0.01M citric acid to pH 6.5). The pool was diluted to the same condictivity as the equilibrating buffer, adjusted to pH 6.5, and then applied to the column. The completely adsorbed enzyme was eluted with the same buffer admixed with phosphate-citrate buffer (0.15M $Na_2HPO_4$ titrated to pH 6.5 with 0.15M citric acid), thereby yielding a linear gradient in buffer concentration. Fractions were collected and analysed as before. The peak fractions showed a specific activity of about 350,000 PU/g.

In sodium dodecyl sulphate polyacrylamide gel electrophoresis (S. G. Braun et al., J. Virology vol. 10 (1972) 221) the contents of the fraction with highest activity exhibited in single protein band corresponding to MW about 100,000 Dalton. The protein has a pI of 5.0 as determined by isoelectric focusing on "LKB Ampholine PAG" plates (following the instructions given by LKB-Produkter AB, Sweden).

ENZYME CHEMICAL PROPERTIES

The immunochemical test results commented on above about partial immunological identity for the debranching enzymes produced by different strains of *Bacillus acidopullulyticus* is reflected in measurable differences in enzyme chemical properties. A significant degree of strain dependency has been found to exist within the debranching enzyme product of this invention. Therefore, the term debranching enzyme is employed herein to refer to the enzyme from some particular strain. The term debranching enzyme product is employed herein to refer in a generic sense to any and/or all of the individual debranching enzymes from *Bacillus acidopullulyticus.*

In most instances the differences in enzyme chemical properties from the properties of the debranching enzyme produced by type strain NCIB 11607 are minor, e.g. being comparable to experimental error differences. The debranching enzyme of NCIB 11611 has a different isoelectric point from that of the type strain debranching enzyme, but otherwise has about the same properties.

The differences between the debranching enzymes produced by the strains herein disclosed, all of which constitute the preferred strains for practice of this invention, are representative of the full range of differences found in the enzymes produced by all strains of *Bacillus acidopullulyticus* tested for production of a debranching enzyme product.

One instance of strain specificity is particularly noteworthy. The strain NCIB 11639 produced a mixture of debranching enzymes. One enzyme, present in minor proportion, was immunochemically identical to the debranching enzyme from the type strain. A second debranching enzyme, present in major proportion, was partially identical immunochemically therewith. In this instance, the two debranching enzymes produced by the strain exhibited sufficent divergence in enzyme chemical properties as to qualify them as being different enzymes (according to enzymology standards), but such a view is neither offered nor disputed here. It so happens that the enzyme chemical properties of the major component debranching enzyme produced by NCIB 11639 are superior, and such enzyme is a most preferred mode of the debranching enzyme product of this invention. Curiously enough a non-preferred strain not herein exemplified produced only this debranching enzyme, and no detectable amounts of the type strain enzyme.

Notwithstanding the differences that exist between the debranching enzymes produced by individual strains of *Bacillus acidopullulyticus*, the debranching enzyme product from *Bacillus acidopullulyticus*, in a generic to them all sense, is superior to the known pullulanases for exhibiting good thermostability at 60° C., for having a pH optimum in the range of pH 3.5–5.5, and for having an activity optimum at 60° C. to 65° C.

To illustrate the variations enzyme to enzyme that have been found within the enzyme product of this invention the following test results are provided below.

A. Isoelectric point and inhibition by treatment with p-Hydroxymercuribenzoate (PMB).

| Strain No. | Isoelectric Point pI | Inhibition PMB |
|---|---|---|
| NCIB 11607 | 5.0 | + |
| NCIB 11610 | 5.0 | + |
| NCIB 11611 | 5.5 | + |
| NCIB 11636 | 5.0 | + |
| NCIB 11637 | 5.0 | + |
| NCIB 11639 | 5.6 | − |

B. Immunochemical identity with debranching enzyme from type strain NCIB 11607.

| Strain No. | Identity |
|---|---|
| NCIB 11610 | yes |
| NCIB 11611 | partial |
| NCIB 11636* | partial |
| NCIB 11637* | partial |
| NCIB 11638** | yes |
| NCIB 11639 | partial |
| NCIB 11647** | yes |

*The debranching enzymes from 11636 and 11637 are identical immunochemically.
**Strains 11638 and 11647 are mutants of type strain 11607.

For many of the tests reported hereinafter the debranching enzyme produced by mutant strains 11638 and 11647 was employed in lieu of that from 11607.

C. Pullulanase activity as a function of the temperature (other reaction conditions being those described above for assay of pullulanase activity). Activity is reported as percent of activity, at 60° C.

| Strain NCIB | 55° C. | 60° C. | 65° C. | 70° C. |
|---|---|---|---|---|
| | | percent | | |
| NCIB 11611 | 94 | 100 | 91 | 26 |
| NCIB 11647 | 90 | 100 | 84 | 7 |
| NCIB 11639 | 82 | 100 | 104 | 97 |
| NCIB 11637 | 78 | 100 | 78 | — |

D. Comparison of thermostability of enzymes from NCIB 11639 and NCIB 11647 in glucose solution (about 30 percent dry substance) at varying pH and temperature levels.

The enzyme product was dissolved in or diluted with deionized water to give a solution containing approximately 3 PU per ml. Samples were prepared by mixing the enzyme solution (1 ml) with 0.1M citrate-phosphate buffer of chosen pH (1 ml) and dissolving glucose (0.8 g) therein. After incubation of the samples at the chosen temperature for 72 hours the residual amylopection debranching activity (vide infra) was determined. The residual activity is reported as percent of activity of identical samples kept at 4° C.

| | Enzyme from Strain No. | | | |
|---|---|---|---|---|
| | 11639 | | 11647 | |
| | Temp. | | | |
| pH | 59° C.–60° C. | 63° C.–64° C. | 59° C.–60° C. | 63° C.–64° C. |
| 3.65 | 55 | 9 | 0 | 0 |
| 4.1 | 90 | 75 | 0 | 0 |
| 4.6 | 90 | 80 | 70 | 7 |
| 5.0 | 90 | 90 | 85 | 67 |
| 5.3 | 90 | 90 | 75 | 67 |
| 5.5 | 90 | 90 | 65 | 50 |

Comparison of thermostability of enzyme from NCIB 11638 and isoamylase in glucose solution (about 30 percent dry substance).

A solution of the enzyme product prepared in the following Example 1 was prepared as described above. After incubation of samples as described above for 3 days at 50° C. and 60° C. the residual amylopectin debranching activity was determined. A comparative test was conducted with Pseudomonas isoamylase (Hayashibara Biochemical Laboratories, Japan, containing 500,000 isoamylase units (IA) per g) diluted to 300 IA per ml. The results are presented in the following table.

| | | Percent residual activity after 3 days | |
|---|---|---|---|
| | | Debranching enzyme of | |
| Temperature °C. | pH after incubation | NCIB 11638 | Isoamylase |
| 50 | 4.5 | 109 | 75 |
| | 4.9 | 100 | 68 |
| 60 | 4.9 | 89 | 1 |
| | 5.2 | 85 | 3 |

Assay of Amylopectin Debranching Activity:

Hydrolysis of the alpha-1,6-bonds of amylopectin causes an increase in the colour intensity (as measured at 610 nm) of the blue iodine-amylopectin complex. This increase is dependent on the amount of alpha-1,6-bonds hydrolysed.

The enzyme solution (1 ml), diluted in deionized water to a concentration corresponding to 1-2 PU and 20-40 IA per ml for debranching enzyme and isoamylase, respectively, is mixed with acetate buffer (1 ml of 0.5M, pH 4.5) and a 1 percent solution (5 ml) of amylopectin (CPC, SNOWFLAKE 04201 starch). The mixture is incubated for 30 minutes at 50° C. An aliquot (0.5 ml) is mixed with 15 ml of 0.02N $H_2SO_4$ and 0.5 ml of iodine solution (0.01M iodine in 0.2 percent potassium iodide).

After 15 minutes at room temperature the optical density at 610 nm is compared with that of a blank run with heat inactivated enzyme.

Figure 1:
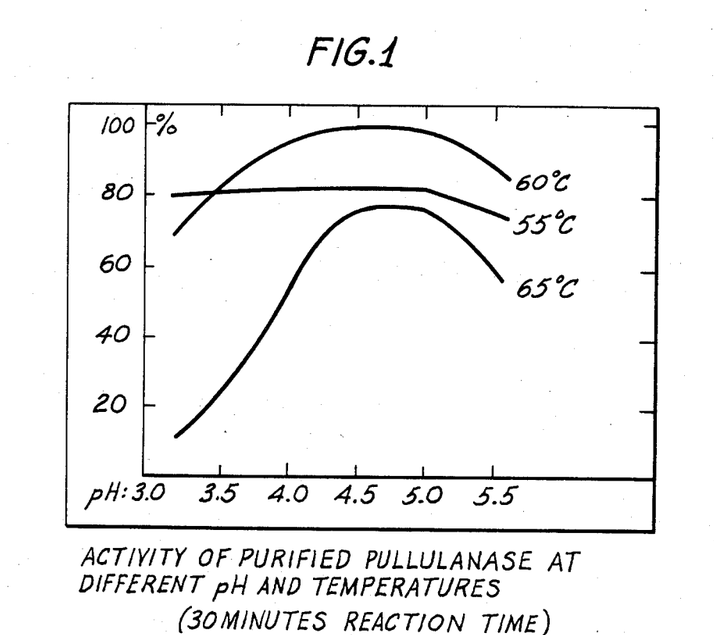
FIG. 1 illustrates the relative activity of the debranching enzyme of NCIB 11607 plotted against pH at 55° C., 60° C., and 65° C.
Figure 2:
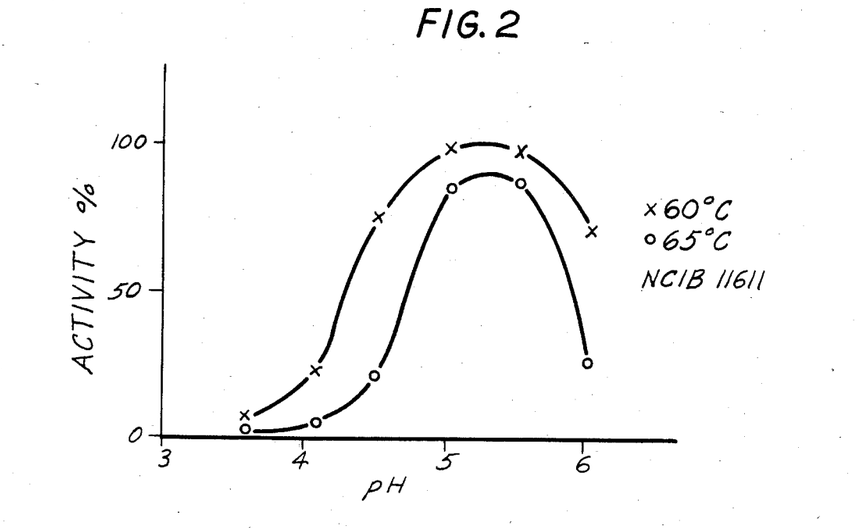
FIG. 2 illustrates the relative activity of debranching enzyme of NCIB 11611 plotted against pH at 60° C. and 65° C.
Figure 3:
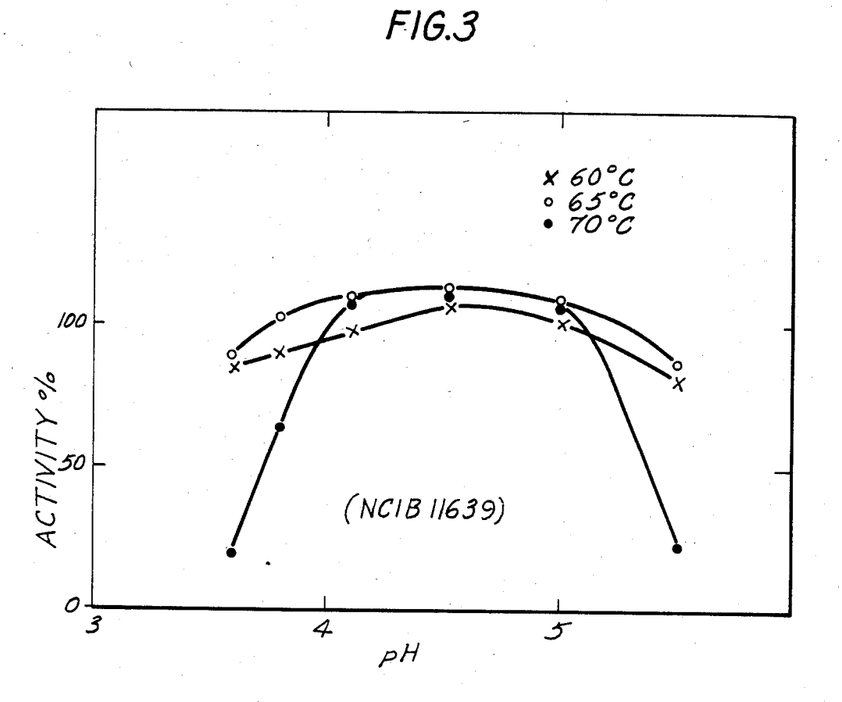
FIG. 3 illustrates the relative activity of the debranching enzyme of NCIB 11639 plotted against pH at 60° C., 65° C., and 70° C.

E. The dependence of the activity of the debranching enzyme product of this invention on pH in the range of 3.5-5.5 at different temperature levels was determined by the method for determination of pullulanase activity described above, using a reaction mixture of which pH and temperature were adjusted to predetermined values.

Reference is now made to the attached drawing wherein.

Immunochemical Properties

Monospecific antiserum was generated by immunizing rabbits with purified debranching enzyme according to the method described by N. H. Axelsen et al., A Manual of Quantitative Immunoelectrophoresis (Oslo 1973) chap. 23. The debranching enzyme was prepared by cultivating the strain NCIB 11638 (cf. Example 1 hereinafter provided) and purified as described above.

The immunogen (0.5 ml of a solution containing 18 PU per ml, corresponding to 0.15 mg of protein per ml) was mixed with Freund's adjuvant (0.5 ml) and injected subcutaneously into rabbits every second week. Antiserum was obtained after a total immunization period of 8 weeks and immunoglobulin was prepared therefrom as described by N. H. Axelsen et al., supra.

Two samples of the crude debranching enzyme product derived from the same strain (NCIB 11638), e.g., as obtained according to Example 1 hereinafter (each sample containing 10 PU per ml), were subjected to crossed immunoelectrophoresis according to the same authors (chap. 3) First dimension: 1 percent agarose in TRIS-boric acid buffer (20 mM, pH 8.6); electrophoresis at 15° C., 8 volts per cm for 2 hours. Second dimension: Same agarose gel as above containing the immunoglobulin (100 μl); electrophoresis at 15° C., 1 volt per cm for 16 hours.

One plate, stained with Coomassie Brilliant Blue, gave a single peak of immunoprecipitate. The second plate was used for detecting the enzyme by means of an overlayer technique. The plate was covered with a gel containing pullulan and agarose (1 percent of each) in maleate buffer (0.1M, pH 5). After incubation for 2 hours at 50° C. the remaining pullulan was precipitated with acetone whereby a clearing zone indicating pullulan hydrolysis became visible. Comparison of the two electropherograms showed that the clearing zone and the stained immunoprecipitate were superimposable, thus demonstrating the monospecificity of the immunoglobulin generated against the debranching enzyme produced by the strain NCIB 11638.

The immunological properties of the debranching enzyme derived from each of the other deposited strains were compared with those of the enzyme from NCIB 11638 by crossed immunoelectrophoresis, using the above prepared immunoglobulin as reference antiserum. The immunograms so obtained demonstrated the already described identity or partial identity with respect to immunochemical properties of all specimens of debranching enzyme investigated. With respect to the meaning of the terms "immunochemical identity" and "partial immunochemical identity", reference is made to the above cited monograph by N. H. Axelsen et al., chapters 10 and 11, respectively.

The following examples are presented as illustrative embodiments of this invention and are not intended as specific limitations thereof.

EXAMPLE 1

Preparation of Debranching Enzyme Product from Strain NCIB 11638

The strain NCIB 11638 (which is a mutant of NCIB 11607) was propagated on agar slants for 2 days at 37° C. The agar medium was prepared from the basal medium (p.9) by addition of amylopectin (0.5 percent of Snow Flake waxy starch CPC) and 2 percent Bacto-agar (Difco).

The cells were suspended in sterile water and transferred to a 2 liter laboratory fermentor (Eschweiler, Kiel, West Germany) containing 1 liter of the following medium:

| Yeast extract | 0.2 percent |
|---|---|
| Corn steep liquor (50% dry substance) | 1.0 — |
| $MgSO_4.7H_2O$ | 0.025 — |
| $K_2HPO_4$ | 0.05 — |
| $(NH_4)_2SO_4$ | 0.125 — |
| $CaCl_2.2H_2O$ | 0.025 — |
| PLURONIC L 61 | 0.1 — |
| dissolved in tap water | |

The pH was adjusted to 5.5 prior to autoclaving at 130° C. for 30 minutes. Glucose was autoclaved separately and added to a final concentration of 1 percent.

During the cultivation pH was kept at 5.5±0.2 by addition of sulphuric acid (2 percent solution). The temperature was 30.0±0.1° C., and the aeration rate 650 ml per minute (±10 percent).

After 22 hours of cultivation, substrate exchange was initiated at a dilution rate of 0.03 hour$^{-1}$. After a further 36 hours steady state fermentation conditions were reached at a cell density of about 4 g of dry cells per liter (corresponding to an absorbance of 8 at 450 nm). The pullulanase activity was 7.5 PU per ml.

During 6 days of steady state continous fermentation, 4,000 ml of culture liquid was collected in a chilled flask. The cells were removed by centrifugation for 30 minutes at 2,300 rpm, and the supernatant, containing 5.1 PU per ml, was concentrated by ultrafiltration through a G-600 membrane using a standard laboratory outfit (supplied by Sartorius). The volume of this concentrate (800 ml) was further reduced in a Büchi rotating evaporator at 45° C. The final concentrate (76 ml) so obtained was frozen and lyophilized, thereby yielding a dry powdered product (6.8 g) having an activity of 1150 PU per g.

EXAMPLE 2

Preparation of Debranching Enzyme Product from Strain NCIB 11647

Run A

The fermentation was conducted in a stainless steel pilot fermentor (total capacity 550 liters, 70 cm diameter) provided with two 6-blade, 24 cm diameter, turbine agitators and with accessories required for continuous fermentation, including equipment for the maintenance of constant pH and temperature. The fermentor was charged with a medium (300 liters) of the following composition:

| | | |
|---|---|---|
| Soy bean meal | 25 | g |
| Corn steep liquor (50% dry solids) | 5 | — |
| Potato starch | 8.3 | — |
| $KH_2PO_4$ | 1.7 | — |
| $(NH_4)_2SO_4$ | 1.0 | — |
| Bacterial amylase BAN 120 L | 0.013 | ml |
| Antifoam agent PLURONIC L 61 | 0.233 | — |
| Tap water to | 1 | liter |

The pH of the medium was adjusted to 5.8 with sodium hydroxide solution. The starch was liquefied by raising the temperature gradually from 60° C. to 90° C. in the course of 50 minutes followed by sterilization at 121° C. for 60 minutes.

A culture of the strain NCIB 11647, grown for 4 days in a Fernbach culture flask on the same nutrient agar substrate as used in Example 1, was used for inoculation of 300 liters of medium. The fermentation was conducted at 29° C.-31° C., the agitator speed being 100 r.p.m. and the aeration rate 150 standard liters per minute at a pressure of 0.5 bar. Starting at 33.5 hours after inoculation, a sterile medium of the same composition as above and prepared in the same manner was fed continously to the culture at a rate of 15 liters per hour. When a volume of 375 liters was reached, automatic withdrawal of culture liquid was initiated. Approximately 30 hours after inoculation vigorous growth was observed by microscopy and as indicated by increased generation of $CO_2$.

Collection of culture broth commenced at a culture age of 73 hours. The debranching enzyme activity had then increased to above 10 PU per ml. During the period of from 115 hours to 210 hours an approximately steady state was maintained at an enzyme concentration corresponding to between 50 and 76 PU per ml, the pH of the broth varying between 5.4 and 5.9.

All subsequent operations were conducted at pH 5.5-5.7. The fermentation broth collected during 110 hours (1650 liters) was filtered on a rotary vacuum filter (2.5 m²) coated with diatomaceous earth filter aid. The filtrate was concentrated and freed from low molecular weight compounds by ultrafiltration using a DDS (7 m²) module (supplied by DDS, Copenhagen, Denmark) provided with a cellulose acetate membrane, type 600. The final concentrate (70 liters) contained 9.4 percent dry substance.

Further concentration (to a volume of 21 liters), was effected in a rotary vacuum evaporator. An additional pressure filtration, using the same filter aid as above, gave an enzyme concentrate (15.5 kg, containing 28.8 percent dry substance) with an activity of 1500 PU per g.

Run B

The fermentation was conducted in a stainless steel fermenter with a total volume of 2500 liters. A working volume of 1800-2200 liters was used.

The medium contained:

| | |
|---|---|
| Yeast extract paste (80% D.S.) | 3 g |
| Corn steep liquor (50% D.S.) | 15 g |
| Potato starch sirup, liquified (40% w/v) | 17.3 ml |
| $KH_2PO_4$ | 1.0 g |
| $(NH_4)_2SO_4$ | 1.3 g |
| $CaCl_2, 2H_2O$ | 0.25 g |
| $MgSO_4, 7H_2O$ | 0.25 g |
| PLURONIC L 61 | 0.1 ml |
| Tap water to | 1 liter |

The pH of the medium was adjusted to 5.4-5.6 with sodium hydroxide solution. The starch was liquefied with 2 ml of TERMAMYL L-60 per kg of dry starch at 90° C. for 60 minutes. The liquefaction was terminated by addition of citric acid (1 g per of dry starch) followed by heating to boiling.

A culture of strain NCIB 11647, grown for 3 days on the agar substrate used in Example 1 was used to inoculate 310 liters of medium in a 550 liter seed fermenter. The fermentation was conducted at 35° C., the agitator speed being 150 r.p.m. and the aeration rate 150 standard liters per minute at a pressure of 0.5 bar.

When this seed culture was 42 hours old, it was used to inoculate the 2500 liter fermenter containing 1870 liters of medium. The temperature in the 2500 liter fermenter was maintained at 29°-31° C. The agitator speed was set at 70 r.p.m. The air flow was adjusted to 700 standard liters per minute and the pressure to 0.5 bar. From 11 hours till 40 hours after inoculation, sterile medium of the same composition as above was fed to the fermenter at a rate of 80-95 liters per hours. When the broth volume reached 2200 liters, culture was automatically withdrawn.

Approximately 10 hours after inoculation vigorous growth was observed by microscopy and by methylene blue reduction. The pullulanase activity reached 9 PU per g at 23 hours and 30 PU per g at 35 hours after inoculation. The pH of the culture varied between 5.6 and 6.4.

From 23 hours after inoculation, the culture broth was collected and cooled. This collected broth was mixed with the residual content of the fermenter when the experiment was terminated at 40 hours after inoculation. The mixture was used for recovery experiments.

To 1200 liters of fermentation broth with an activity of 30 PU per g was added sodium hydrogen sulfite (2.4 kg) and calcium chloride (12 kg). After adjustment of pH to 6.0 with sodium hydroxide flocculation was performed with 1 kg of Filtrafloc XL01 (International Water Consultant B.V.) and 0.06 kg of Nalco 673 (Deutsche Nalco-Chemie GmbH).

The sludge was removed by vacuum drum filtration with diatomaceous earth as precoat, and pH reduced to 4.9 with acetic acid. After a polishing filtration to remove traces of precoat, the filtrate was reduced to 12.5 kg by ultrafiltration using a DDS 35 module provided with GR60 membranes.

Additional pressure filtration with diatomaceous earth and germ filtration gave 11.8 kg of enzyme concentrate (containing 10% of dry substance) with an activity of 1600 PU per g.

EXAMPLE 3

Preparation of debranching enzyme product from strains NCIB 11610, NCIB 11636 and NCIB 11637

The strains were propagated and the fermentations conducted in the same manner as that described in Example 1. Maltose (0.5 percent) was used instead of glucose as the carbon source. Mean values of other parameters of the fermentations will appear from the following Table 1.

TABLE 1

|  | NCIB 11610 | NCIB 11636 | NCIB 11637 |
|---|---|---|---|
| Dilution rate, $hour^{-1}$ | 0.07 | 0.057 | 0.06 |
| Absorbance at 450 nm | 9.2 | 8.3 | 9.1 |
| Dry weight of bacteria, g/liter | 5.4 | 4.9 | 3.8 |
| Debranching enzyme activity, PU/ml | 0.80 | 0.25 | 0.11 |

The culture broths were collected and the debranching enzyme products were recovered essentially as described in Example 1. Details of the work-up procedure will appear from the following Table 2.

TABLE 2

| Strain NCIB No. | Culture liquid ml | Supernatant ml | Supernatant PU/ml | Lyophilized product g | Lyophilized product PU/g |
|---|---|---|---|---|---|
| 11610 | 5316 | 5110 | 0.37 | 7.5 | 69.2 |
| 11636 | 1497 | 1405 | 0.08 | 4.4 | 14.4 |
| 11637 | 4856 | 4790 | 0.04 | 6.0 | 12.2 |

EXAMPLE 4

Run A

Preparation of Debranching Enzyme Product from strain NCIB 11639

Propagation of strain NCIB 11639, incubation and fermentation was conducted as described in Example 1.

The fermentation medium had the following composition:

| *Soy bean meal extract | 2.0 percent |
|---|---|
| Corn steep liquor | 0.5 — |
| $MgSO_4, 7H_2O$ | 0.025 — |
| $K_2HPO_4$ | 0.1 — |
| $(NH_4)_2SO_4$ | 0.05 — |
| Amylase-liquefied starch (Dextrose equiv. 11) | 0.5 — |
| PLURONIC L 61 dissolved in tap water | 0.1 — |

*Extraction of soy bean meal solubles at pH 4.5 and 50° C. for 4 hours. Insoluble material was removed by centrifugation.

The pH was adjusted to 4.0 before autoclaving at 130° C. for 60 minutes.

During the cultivation pH was kept at 5.6±0.1 by addition of a sodium hydroxide solution (2 percent). The temperature was 30.0°±0.1° C. and the aeration rate 320 ml/min at a stirrer speed of 530–565 rpm. The fermentation was run continuously at a dilution rate of 0.03–0.05 $hr^{-1}$ for 186 hours when collection of overflowing culture liquid was started. Culture liquid (5100 ml, 0.47 PU/ml) was collected over dry ice for an additional 97 hours under the following conditions:

| Dilution rate | 0.049 ± 0.008 $hr^{-1}$ |
|---|---|
| $OD_{450}$ | 10.6 ± 1.1 |
| Cell density | 2.9 ± 1.5 g/l |
| Debranching enzyme activity | 0.5 ± 0.1 PU/ml |

The cells were removed as described in Example 1. The supernatant was filtered on a Whatman GFA glass filter (11 cm) and then concentrated to 200 ml on an Amicon DC 2 hollow fibre module provided with an H1P10 membrane. Turbidity was removed on the GFA filter and the filtrate further concentrated on the Amicon module using a 202-DDS 600 membrane (DDS, Copenhagen, Denmark) to yield of final concentrate (30 ml) with an activity of 65 PU/ml. The concentrate was stored deepfrozen.

Run B

Preparation of Debranching Enzyme Product from Strain NCIB 11777

The fermentation was conducted in a stainless steel fermenter with a total volume of 550 liters. A working volume of 340–435 liters was used.

The medium contained:

|  | Medium A | Medium B |
|---|---|---|
| Yeast extract paste (80% D.S.) | — | 3 g |
| Soy bean meal | 25 g | — |
| Corn steep liquor (50% D.S.) | 5 g | 15 g |
| Potato starch sirup, liquified (40% w/v) | 20 ml | 17.5 ml |
| $KH_2PO_4$ | 1.8 g | 1.0 g |
| $(NH_4)_2SO_4$ | 1.0 g | 1.35 g |
| $CaCl_2, 2H_2O$ | — | 0.25 g |
| $MgSO_4, 7H_2O$ | — | 0.25 g |
| PLURONIC L61 | 0.1 ml | 0.1 ml |
| Tap water to | 1 liter | 1 liter |

The pH of the media was adjusted to 5.4–5.6 with sodium hydroxide solution. The starch was liquefied with TERMAMYL L-60 (2 ml per kg of dry starch) at 90° C. for 60 minutes. The liquefaction was terminated by addition of citric acid (1 g per kg of dry starch) and heating to boiling.

A culture strain NCIB 11777, grown for 2 days in a Fernbach culture flask on the same nutrient agar substrate as used in Example 1, was used to inoculate 58 liters of medium A in a 70 liter seed fermenter. The fermentation was conducted at 35° C., the agitator speed being 107 r.p.m. and the aeration rate 30 standard liters per minute at 0.5 bar.

When this seed culture had reached the age of 108 hours, it was used to inoculate the 550 liter fermenter containing 340 liters of medium A. The temperature in the 550 liter fementer was maintained at 29°–31° C. The agitator speed was set at 120 r.p.m. The air flow was adjusted to 150 standard liters per minute at a pressure of 0.5 bar. From 44 hours till 194 hours sterile medium A was fed to the fermenter at a rate of 14–19 liters per hour. When the broth volume reached 435 liters, culture fluid was automatically withdrawn.

From 194 hours after inoculation till termination of the experiment at 525 hours, medium B was fed to the fermenter at a rate of 11–19 liters per hour. The volume was maintained at 435 liters as above.

Approximately 38 hours after inoculation vigorous growth was observed by formation of $CO_2$ and by microscopy. The pullulanase activity reached 0.2 PU per ml at 69 hours of growth and stayed at this level till the change of medium. At 219 hours after inoculation the pullulanase activity reached more than 1.4 PU per ml. The activity increased during the experiment to a maximum of 3.2 PU per ml at 495 hours after inoculation. The pH of the culture varied between 5.4 and 5.8. From 225 hours till 312 hours, culture broth was collected and chilled with ice-water.

1450 liters of fermentation broth (with an activity of 1.73 PU per g) were flocculated with 15 kg of calcium chloride, 1 kg of Filtrox XL01 and 0.25 kg of Nalco 673 at pH 6.0.

The sludge was removed by centrifugation, and the final haze eliminated by filtration on Supra 100 filterplates with diatomaceous earth as filter aid.

The filtrate was adjusted to pH 4.8 with acetic acid and then concentrated by using a DDS 35 module provided with GR60 membranes. The final concentrate (15 kg) contained 10.6 percent of dry substance.

Additional pressure filtration with diatomaceous earth gave an enzyme concentrate (12.8 kg, containing 9.8 percent of dry substance) with an activity of 95 PU per g.

EXAMPLE 5

100 kg of corn starch (Globe® 03430, CPC) were slurried with tap water containing 100 ppm $Ca^{++}$ and the volume adjusted to 225 liters. The pH was adjusted to 6.3 and 135 g of TERMAMYL® 60 L (NOVO Industri A/S, Denmark) were added.

This suspension was continuously pumped through a jet cooker (Hydro-Thermal Corp. Milwaukee) where it was heated to 105° C. by direct steam injection and maintained at 105° C. for five minutes. The liquefied starch suspension was flash-cooled and pumped over into a saccharification tank where it was held for about 1 hour at 95° C.

The pH of the liquefied starch was adjusted to 4.0 at 95° C. to stop the reaction and the batch was then spray-dried without purification. The DE of the spray-dried maltodextrin was 6.

Substrates for saccharification were prepared by redissolving suitable amounts of this maltodextrin in deionized water and making up to approximately 30 percent D.S. Aliquots of this substrate were then taken and heated to 60° C. and the pH adjusted to 4.8. Different amounts of debranching enzyme from NCIB 11647 were then added together with glucoamylase (Amyloglucosidase Novo 150, 150 AG units/ml). The reaction mixtures were sampled at set time intervals and the % dextrose in each sample determined by HPLC. The following results were obtained:

| Debranching Enzyme PU units/g D.S. | Glucoamylase AG units/g D.S. | Reaction time (h) | pH | % Dextrose |
|---|---|---|---|---|
| 0 (control) | 0.225 | 72 | 4.1 | 95.8 |
|  | 0.225 | 96 | 4.1 | 95.9 |
| 0 (control) | 0.113 | 72 | 4.6 | 93.3 |
|  | 0.113 | 96 | 4.3 | 94.4 |
| 0.01 | 0.150 | 96 | 4.3 | 96.1 |

-continued

| Debranching Enzyme PU units/g D.S. | Glucoamylase AG units/g D.S. | Reaction time (h) | pH | % Dextrose |
|---|---|---|---|---|
| 0.1 | 0.113 | 96 | 4.4 | 95.9 |
| 0.5 | 0.113 | 96 | 4.4 | 96.7 |
| 1.0 | 0.113 | 72 | 4.6 | 97.0 |
| 2.0 | 0.113 | 72 | 4.7 | 97.3 |
| 4.0 | 0.113 | 72 | 4.7 | 97.4 |

These results indicate that when debranching enzyme is used together with glucoamylase, the same dextrose level can be obtained with half the glucoamylase dosage used in the control when a debranching enzyme dosage of 0.1 PU/g D.S. is used.

If the debranching enzyme dosage is increased the maximum obtainable dextrose level also increases.

EXAMPLE 6

Aliquots of the substrate prepared as in Example 5 were heated to 55° or 60° C. and the pH adjusted to 4.9. An amount of glucoamylase corresponding to 0.113 AG/g D.S. and an amount of the same debranching enzyme corresponging to 1.2 PU/g D.S. were added. The reaction mixtures were sampled and analyzed as in Example 5.

The following results were obtained:

| Temperature °C. | Reaction time (hours) | Dextrose % |
|---|---|---|
| 55 | 24 | 84.5 |
|  | 48 | 96.5 |
|  | 72 | 97.1 |
|  | 96 | 97.3 |
| 60 | 24 | 90.0 |
|  | 48 | 96.8 |
|  | 72 | 97.0 |
|  | 96 | 97.3 |

These results confirm that the debranching enzyme is sufficiently heat stable to be used at 60° C.

EXAMPLE 7

A spray-dried maltodextrin substrate with a DE of 5 was prepared according to the method described in Example 5.

Aliquots of this substrate were heated to 60°, 62.5° and 65° C. and the pH adjusted to 4.9. An amount of glucoamylase corresponding to 0.113 AG/g D.S. and an amount of debranching enzyme from NCIB 11647 corresponding to 1 PU/g D.S. were added. Control saccharifications to which an amount of glucoamylase corresponding to 0.225 AG/g D.S. had been added, but without debranching enzyme, were also included.

The reaction mixtures were sampled and analysed as in Example 5. The dry substance (D.S.) during saccharification was 31 percent.

| Debranching Enzyme PU/g D.S. | Glucoamylase AG/g D.S. | Temperature °C. | Reaction time (hours) | Dextrose % |
|---|---|---|---|---|
| 0 | 0.225 | 60 | 24 | 92.1 |
|  |  |  | 48 | 95.3 |
|  |  |  | 72 | 96.0 |
|  |  |  | 96 | 96.0 |
| 1 | 0.113 | 60 | 24 | 88.9 |
|  |  |  | 48 | 96.1 |
|  |  |  | 72 | 96.7 |
|  |  |  | 96 | 97.0 |

| Debranching Enzyme PU/g D.S. | Glucoamylase AG/g D.S. | Temperature °C. | Reaction time (hours) | Dextrose % |
|---|---|---|---|---|
| 0 | 0.225 | 62.5 | 24 | 92.1 |
|   |       |      | 48 | 95.1 |
|   |       |      | 72 | 95.8 |
|   |       |      | 96 | 96.1 |
| 1 | 0.113 | 62.5 | 24 | 89.3 |
|   |       |      | 48 | 95.9 |
|   |       |      | 72 | 96.8 |
|   |       |      | 96 | 97.0 |
| 0 | 0.225 | 65   | 24 | 91.4 |
|   |       |      | 48 | 94.1 |
|   |       |      | 72 | 95.2 |
|   |       |      | 96 | 95.4 |
| 1 | 0.113 | 65   | 24 | 82.9 |
|   |       |      | 48 | 89.9 |
|   |       |      | 72 | 92.8 |
|   |       |      | 96 | 93.6 |

These results indicate that saccharification with debranching enzyme and glucoamylase may be carried out at 60°-62.5° C. At 65° C. the results are inferior, which may be due to glucoamylase instability at that temperature.

EXAMPLE 8

Aliquots of the substrate prepared as in Example 5 were heated to 60° C. and the pH adjusted to 4.5, and 4.8. An amount of glucoamylase corresponding to 0.113 AG/g D.S. and an amount of the same debranching enzyme corresponding to 1 PU/g D.S. were added. The reaction mixtures were sampled and analyzed as in Example 5. The following results were obtained:

| pH | Reaction time (hours) | % Dextrose |
|---|---|---|
| 4.5 | 24 | 89.6 |
|     | 48 | 96.6 |
|     | 72 | 96.8 |
|     | 96 | 96.9 |
| 4.8 | 24 | 89.0 |
|     | 48 | 96.5 |
|     | 72 | 96.8 |
|     | 96 | 97.0 |

These results indicate that similar results can be obtained when saccharifying at pH 4.5 and 4.8.

EXAMPLE 9

A 35 percent D.S. (DE 6) substrate was prepared by dissolving a portion of the maltodextrin prepared as described in Example 5 in deionized water. Aliquots of this substrate were taken and heated to 60° C. and the pH adjusted to 4.3 and 4.8.

An amount of glucoamylase corresponding to 0.113 AG/g D.S. and an amount of purified debranching enzyme from NCIB 11647 (120 PU/mg protein) corresponding to 1 PU/g D.S. was added. The reaction mixtures were sampled and analyzed as in Example 5. The following results were obtained:

| Reaction time (hours) | pH | % Dextrose |
|---|---|---|
| 0 | 4.3 | — |
| 24 | 4.3 | 89.2 |
| 48 | 4.2 | 96.1 |
| 72 | 4.2 | 96.2 |
| 0 | 4.8 | — |
| 24 | 4.5 | 88.4 |
| 48 | 4.5 | 96.0 |
| 72 | 4.4 | 96.2 |

These results indicate that similar dextrose levels can be obtained when saccharification is started at pH 4.3 or 4.8.

EXAMPLE 10

Substrates with different dry solids contents were prepared by dissolving 100 g of the DE 6 maltodextrin from Example 5 in different amounts of deionized water and adjusting the pH's to 4.6 at 60° C. 0.113 AG/g D.S. of glucoamylase and 1 PU/g D.S. of the debranching enzyme of NCIB 11647 were added The reaction mixtures were sampled and analyzed as in Example 5. The following results were obtained:

| % D.S. | % Max. Dextrose |
|---|---|
| 25 | 97.7 |
| 30 | 97.2 |
| 35 | 96.3 |
| 40 | 94.9 |
| 45 | 93.0 |

In a control saccharification without debranching enzyme, the maximum dextrose that could be obtained with this substrate at 60° C., pH 4.5 and 0.225 AG units/g D.S. glucoamylase, and at 30 percent D.S., was 96.3. This means that saccharification may be carried out at a higher solids level when debranching enzyme is used to achieve the same dextrose level so that energy requirements for evaporation will be considerably less.

EXAMPLE 11

A further batch of spray-dried maltodextrin with a DE of 5.0 was prepared according to the procedure outlined in Example 5.

Substrates for saccharification were prepared by redissolving suitable amounts of this maltodextrin in deionized water and making up to approximately 30 percent. Aliquots of this substrate were then heated to 60° C. and the pH adjusted to 5.0.

600 g/ton D.S. beta-amylase (Biozyme M II—Amano Pharmaceutical Co., Ltd, Nagoya, Japan, containing 33.4 beta-amylase units (per g) and different amounts of the debranching enzyme of NCIB 11647 were added and the reaction mixtures sampled after 72 hours. The percent maltose was determined by HPLC. The following results were obtained:

| Debranching enzyme (PU/g D.S.) | % Dextrose | % Maltose |
|---|---|---|
| 0 (control) | 0.3 | 58.7 |
| 0.1 | 0.2 | 63.0 |
| 0.5 | 0.4 | 71.8 |
| 1 | 0.4 | 75.8 |
| 2 | 0.5 | 78.4 |
| 4 | 0.4 | 79.6 |

These results indicate that when debranching enzyme is used in combination with beta-amylase, considerably higher maltose levels can be obtained.

EXAMPLE 12

114 g of Tapioca starch were slurried with 886 ml of deionized water to which had been added 0.5 g calcium chloride. The slurry was cooked by heating to approximately 100° C. and then cooled to 50° C. The pH was adjusted to 5.7 and 0.56 g of Biozyme M II and an amount of the debranching enzyme of NCIB 11647 corresponding to 2 PU/g D.S. were added. The pH was kept constant at 5.5. The reaction mixture was sampled and analyzed by HPLC.

| Reaction time (hours) | % Dextrose | % Maltose |
| --- | --- | --- |
| 24 | 0.5 | 77.4 |
| 48 | 0.6 | 84.4 |

This demonstrates that debranching enzyme can be used together with beta-amylase to produce extra-high maltose syrups.

EXAMPLE 13

A batch of spray-dried maltodextrin with a DE of 7.0 was prepared according to the procedure outlined in Example 5.

Substrates for saccharification were prepared by re-dissolving suitable amounts of this maltodextrin in deionized water and making up to approximately 30% DS. Aliquots of this substrate were then heated to 60° C. and the pH's adjusted to 4.8, 4.5 or 4.0. Two series of parallel saccharafication experiments with the same dosage of glucoamylase, corresponding to 0.113 AG units/g DS were set up. In the first series an amount of debranching enzyme from NCIB 11647 corresponding to 1PU/g DS was added. In the second series an amount of debranching enzyme from NCIB 11777 corresponding to 1PU/g DS was added.

The reaction mixtures were sampled and analysed as in example 5. The dry substance (DS) during saccharification was 31%.

| Debranching enzyme from NCIB 11647 | | |
| --- | --- | --- |
| Reaction time (hours) | pH | % Dextrose |
| 2 | 4.7 | — |
| 24 | 4.5 | 90.3 |
| 48 | 4.4 | 96.9 |
| 72 | 4.3 | 96.9 |
| 96 | 4.3 | 97.0 |
| 2 | 4.4 | — |
| 24 | 4.2 | 90.0 |
| 48 | 4.2 | 96.6 |
| 72 | 4.1 | 96.8 |
| 96 | 4.0 | 96.7 |
| 2 | 4.0 | — |
| 24 | 3.8 | 83.8 |
| 48 | 3.8 | 91.7 |
| 72 | 3.7 | 93.4 |
| 96 | 3.7 | 94.6 |

| Debranching enzyme from NCIB 11777. | | |
| --- | --- | --- |
| Reaction time (hours) | pH | % Dextrose |
| 2 | 4.7 | — |
| 24 | 4.6 | 90.5 |
| 48 | 4.5 | 96.8 |
| 72 | 4.4 | 96.8 |
| 96 | 4.3 | 96.8 |
| 2 | 4.5 | — |
| 24 | 4.3 | 90.8 |
| 48 | 4.2 | 96.9 |
| 72 | 4.2 | 96.9 |
| 96 | 4.1 | 96.9 |
| 2 | 4.1 | — |
| 24 | 3.9 | 90.6 |
| 48 | 3.9 | 96.7 |
| 72 | 3.8 | 96.7 |
| 96 | 3.8 | 96.9 |

These data indicate that similar results can be obtained with the debranching enzymes from NCIB 11647 and NCIB 11777 when starting the saccharification at above a pH of about 4.4. Below a pH of about 4.0 the debranching enzyme from NCIB 11777 unlike the debranching enzyme from NCIB 11647 retains its activity.

EXAMPLE 14

Aliquots of the substrate prepared as in Example 13 were adjusted to pH 4.5 and heated to 60° C. An amount of glucoamylase corresponding to 0.113 AG units/g DS and varying amounts of debranching enzyme obtained from NCIB 11639 were added. The reaction mixture were sampled and analysed as in Example 5.

| Debranching enzyme PU/g DS | Reaction time (h) | pH | % Dextrose |
| --- | --- | --- | --- |
| 0.05 | 24 | 4.2 | 83.7 |
|  | 48 | 4.1 | 93.1 |
|  | 72 | 3.9 | 95.6 |
|  | 96 | 4.0 | 96.0 |
| 0.1 | 24 | 4.2 | 84.7 |
|  | 48 | 4.1 | 94.0 |
|  | 72 | 3.9 | 96.1 |
|  | 96 | 3.9 | 96.0 |
| 0.25 | 24 | 4.2 | 86.9 |
|  | 48 | 4.1 | 95.6 |
|  | 72 | 3.9 | 96.6 |
|  | 96 | 4.0 | 96.6 |
| 0.5 | 24 | 4.2 | 88.0 |
|  | 48 | 4.1 | 96.3 |
|  | 72 | 3.9 | 96.8 |
|  | 96 | 4.0 | 96.7 |
| 1.0 | 24 | 4.2 | 90.8 |
|  | 48 | 4.1 | 96.9 |
|  | 72 | 3.9 | 97.1 |
|  | 96 | 4.0 | 97.1 |
| 2.0 | 24 | 4.3 | 92.8 |
|  | 48 | 4.2 | 97.3 |
|  | 72 | 4.0 | 97.3 |
|  | 96 | 4.0 | 97.1 |

The test results exemplified herein delineate saccharifying conditions that can be recommended for using the debranching enzyme product from *Bacillus acidopullulyticus* at 1-2 PU per g D.S. with glucoamylase to convert 30 percent D.S. (by weight) or higher starch hydrolysate into at least 96 DX, the dry substance concentration and the maximum obtainable DX being inversely related. For example, a 96 DX syrup has been obtained at 40 percent D.S. Only about half of the heretofore usual glucoamylase dosage need be used, a dosage of 0.075-0.15 AG units per g D.S. being recommended. The saccharifying temperature should be at least 60° C. The debranching enzyme from NCIB 11639 appears to be more thermostable than the glucoamylase. The pH is in the range of 3 to 5, preferably 4.0–4.5.

We claim:

1. A debranching enzyme product comprising the debranching enzyme from a strain of Bacillus acidopullulyticus said enzyme being further characterized by:
   (a) immunochemical properties identical or partially identical to those of the debranching enzyme derived from the Bacillus strain NCIB 11607 or NCIB 11639,
   (b) activity optimum, measured by incubation for 30 minutes in acetate buffer of 0.05M at pH 4–5 at about 60° C.,
   (c) pH optimum in the range of 3.5 to 5.5 as determined by incubation for 30 minutes in acetate buffer of 0.05M at about 60° C.,
   (d) a residual activity after 72 hours at 60° C. as measured in a dextrose solution of 30 percent D.S. by weight at pH 5 of at least 50 percent.

2. The debranching enzyme product of claim 1 in which the debranching enzyme activity is in the range of from 10 to 350,000 pullulanase units per g.

3. The debranching enzyme product of claim 2 wherein the activity is in the range of from 100 to 15,000 pullulanase units per g.

4. A process for the preparation of a debranching enzyme which process comprises cultivating in a suitable nutrient medium containing carbon and nitrogen sources and inorganic salts, a debranching enzyme producing strain of a microorganism *Bacillus acidopullulyticus,* and thereafter recovering a debranching enzyme product from the medium, the *Bacillus acidopullulyticus* strain being selected from the group consisting of NCIB 11607, NCIB 11610, NCIB 11611, NCIB 11636, NCIB 11637, and NCIB 11639 and mutants thereof.

5. The process of claim 4 wherein the strain is selected from the group of mutant microorganism strains consisting of NCIB 11638, NCIB 11647, and NCIB 11777.

6. A biologically pure culture of a strain of the microorganism *Bacillus acidopullulyticus* selected from the group consisting of NCIB 11607, NCIB 11610, NCIB 11611, NCIB 11636, NCIB 11637, and NCIB 11639 and mutants thereof.

7. A process for converting starch into syrups containing dextrose and/or maltose, which process comprises conducting the saccharification of starch hydrolysate in the presence of an enzyme system which comprises effective amounts of the novel debranching enzyme product defined in claim 2 and a saccharifying enzyme selected from the group consisting of glucoamylase and beta-amylase.

8. The process of claim 7 further comprising saccharification of a starch hydrolysate of at least 30 percent by weight of dry solids.

9. The process of claim 7 in which the saccharification is conducted in the pH range of from 3.5 to 5.5 at a temperature in the range of from 55° C. to 65° C.

10. The process of claim 7 in which the dosages of glucoamylase and beta-amylase are in the range of from 0.05 to 0.5 AG units and from 0.005 to 0.3 beta-amylase units, respectively, per g of dry solids.

11. The process of claim 7 in which the dosage of debranching enzyme is in the range of from 0.005 to 5 pullulanase units per g of dry solids.

12. In a process for saccharifying a starch hydrolysate of about 30 percent to about 40 percent dry substance to a high DX dextrose syrup with glucoamylase, the improvement which comprises saccharifying at about 60° C. or higher and pH in the range of about 4.0 to about 4.5 to 96 DX or higher by an enzyme mixture comprising a gluco-amylase dosage in the range of from 0.075 to 0.15 AG units per g D.S. and a dosage of the debranching enzyme product defined in claim 2 in the range of 1 to 2 pullulanase units per g D.S.

* * * * *